United States Patent [19]

Lape

[11] Patent Number: 4,661,319

[45] Date of Patent: Apr. 28, 1987

[54] BLOOD TRANSFER ASSEMBLY

[75] Inventor: Larry J. Lape, Sugarland, Tex.

[73] Assignee: Boehringer Mannheim Diagnostics, Inc., Indianapolis, Ind.

[21] Appl. No.: 597,513

[22] Filed: Apr. 6, 1984

[51] Int. Cl.[4] .......................... G01N 1/20; G01N 33/52
[52] U.S. Cl. .................................... 422/68; 73/864.01; 128/770; 222/420; 422/99; 422/100
[58] Field of Search ...................... 422/61, 68, 99, 100, 422/70; 73/864.01; 128/770; 222/420; 356/39

[56] References Cited

U.S. PATENT DOCUMENTS

| | | | |
|---|---|---|---|
| 2,232,029 | 2/1941 | Juchli | 222/420 |
| 2,343,610 | 3/1944 | Apfelbaum | 222/420 |
| 3,500,689 | 3/1970 | Band | 73/864.01 |
| 3,626,929 | 12/1971 | Sanz et al. | 128/770 |
| 4,317,473 | 3/1982 | Gaydos | 222/420 |
| 4,397,956 | 8/1983 | Maggio | 436/34 |

OTHER PUBLICATIONS

Dry Beveling of Micropipette Electrodes, Baldwin, J. of Neurosc. Methods, No. 2, (Apr.) 1980, 153–161.

Primary Examiner—Barry S. Richman
Assistant Examiner—Michael Gzybowski
Attorney, Agent, or Firm—Barnes & Thornburg

[57] ABSTRACT

An apparatus for forming a blood droplet of a controlled, generally uniform size from a finger which has been pricked to draw blood includes a "funnel" member providing an upper edge across which the finger is drawn to deposit blood on a surface down which the blood flows under the influence of gravity to a lower edge terminating at a point. The blood flows toward the point, forms into the droplet at the point, and, owing to gravity and the surface tension of the blood, forms into the substantially uniformly sized droplet which falls onto a test strip positioned beneath the point.

10 Claims, 6 Drawing Figures

BLOOD TRANSFER ASSEMBLY

This invention relates to biological fluid testing instruments, and is particularly useful in an instrument for use by vision-impaired persons for determining the concentration of a medically significant component of their body fluids, such as glucose content of blood.

Various types of equipment are known for conducting what is known as reflected-light photometry, in which the reflectivity of a so-called objective area of a test strip is determined. The objective area is specifically dedicated for the determination of a certain property, for example, concentration of a medically significant component of a biological fluid such as blood or urine. The component which is studied is rendered capable of study through a reaction that occurs on the test strip. The objective area undergoes a reflectivity change as a result of the reaction of a reagent material on the objective area with the component of the biological fluid. This change in reflectivity is evaluated to determine the concentration of the medically significant component in the biological fluid. The utilization of test strips and associated instruments to determine medically significant quantitative parameters is known. High precision instruments for achieving quantitative determinations of this type are available. There is, for example, the REFLOCHECK TM blood glucose monitor available from Boehringer Mannheim Diagnostics, Inc.

The particular problem to which the present invention is addressed is that many such instruments for the quantitative determination of concentrations of medically significant components of biological fluids are used by people whose vision is impaired. An example is the diabetic with failing sight due to diabetes who must monitor his blood glucose.

The use of instruments of this type by people with impaired vision is rendered more difficult by the problems such people have preparing blood samples for reaction on test strips and reading by such instruments. Frequently, vision-impaired users place too little blood, or too much blood, on the test strip resulting in inaccurate instrument readings.

According to the present invention, an apparatus is provided for sequentially forming droplets of a biological fluid of a controlled, generally uniform size from the body of the user of the apparatus. The apparatus includes a first surface across which the biological fluid flows from the body under the influence of gravity. The first surface includes a first edge terminating at a point. A second surface is provided for collecting the droplets of the biological fluid. The second surface is disposed beneath the point to catch a droplet as the biological fluid flows downward along the first surface, collects at the point where it forms into the droplet of the controlled, generally uniform size, and, owing to gravity and the surface tension of the biological fluid, falls toward the second surface as a generally uniformly sized droplet.

Illustratively, the first edge of the first surface is a lower edge of the first surface, and the first surface further includes a second, upper edge situated in vertically spaced-apart relation to the lower edge. The biological fluid is blood and is removed from the body of the user by pricking the skin, "milking" the body surface in the region in which the skin is pricked across the upper edge of the first surface to supply to the first surface a small amount of blood which flows downward across the first surface toward the point, where it forms into the droplet of generally uniform size.

Additionally, according to an illustrative embodiment, the second surface is the surface of the objective area of a test strip, and contains a reagent for a medically significant component of the body fluid. Further according to an illustrative embodiment, the droplet must be of a controlled, generally uniform size to insure an appropriate reaction rate between the reagent and the medically significant component of the body fluid.

BRIEF DESCRIPTION OF THE DRAWINGS

The invention may best be understood by referring to the following description and accompanying drawings which illustrate the invention. In the drawings.

Figure 1:
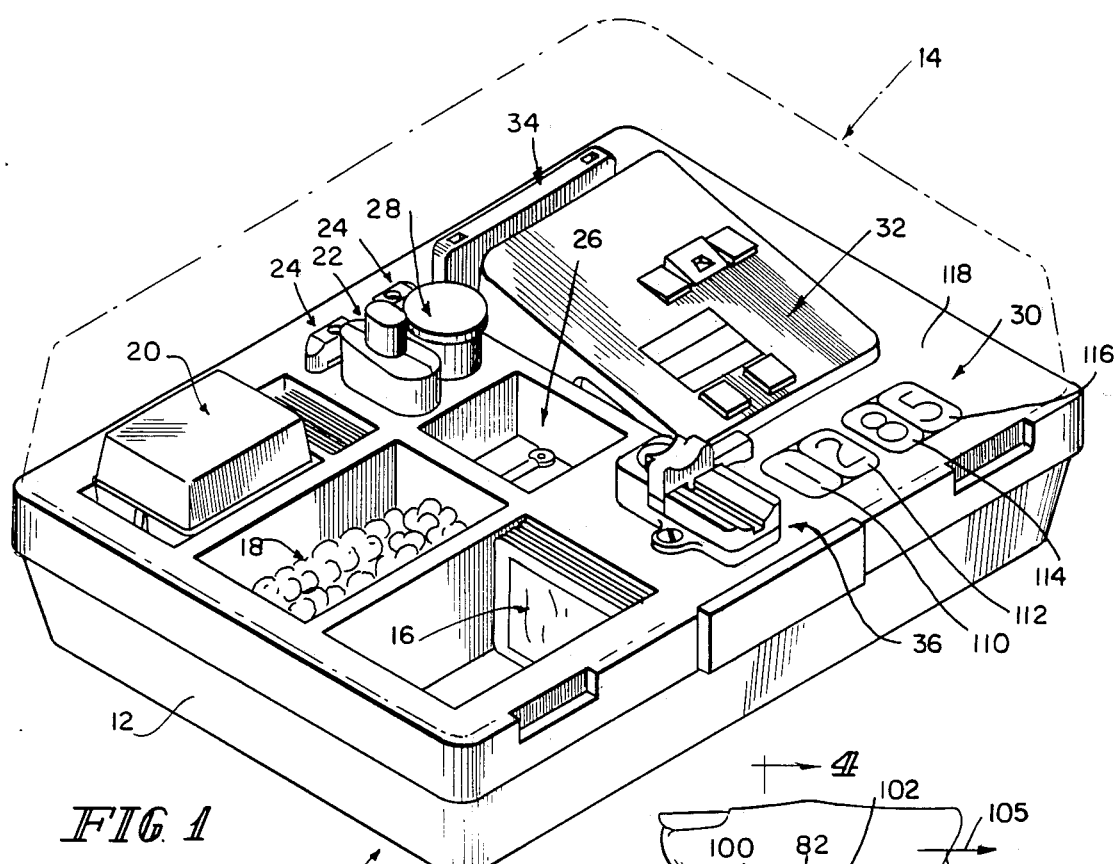
FIG. 1 is a perspective view of a system constructed according to the present invention.

The system of the present invention, as best illustrated in FIG. 1, is housed in a case 10 including a base 12 and a hinged lid 14. The base 12 includes compartments for alcohol wipes 16, cotton balls 18, a plug-in power adapter 20, a tool 22 for puncturing the skin of a user, a plurality of heads 24 for use in conjunction with puncture tool 22 to adjust the depth of the puncture, sterile lancettes 26 for use in conjunction with tool 22 and heads 24 to perform the puncture, a container 28 for reagent-carrying test strips, a calendar 30, a test-strip reading unit 32 such as the REFLOCHECK TM blood glucose monitor, and a cassette tape 34 containing directions for the use of the system. A blood transfer assembly fixture 36 is attached to the base 12 near the front center of the base 12 for easy access by the user.

Figure 3:
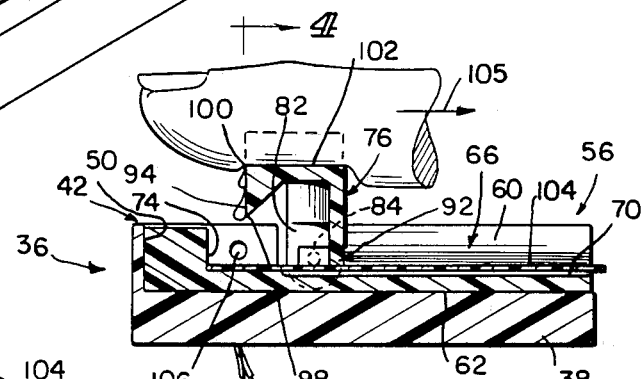
FIG. 3 is a sectional view of the detail of FIG. 2, taken generally along section lines 3—3 of FIG. 2.
Figure 2:
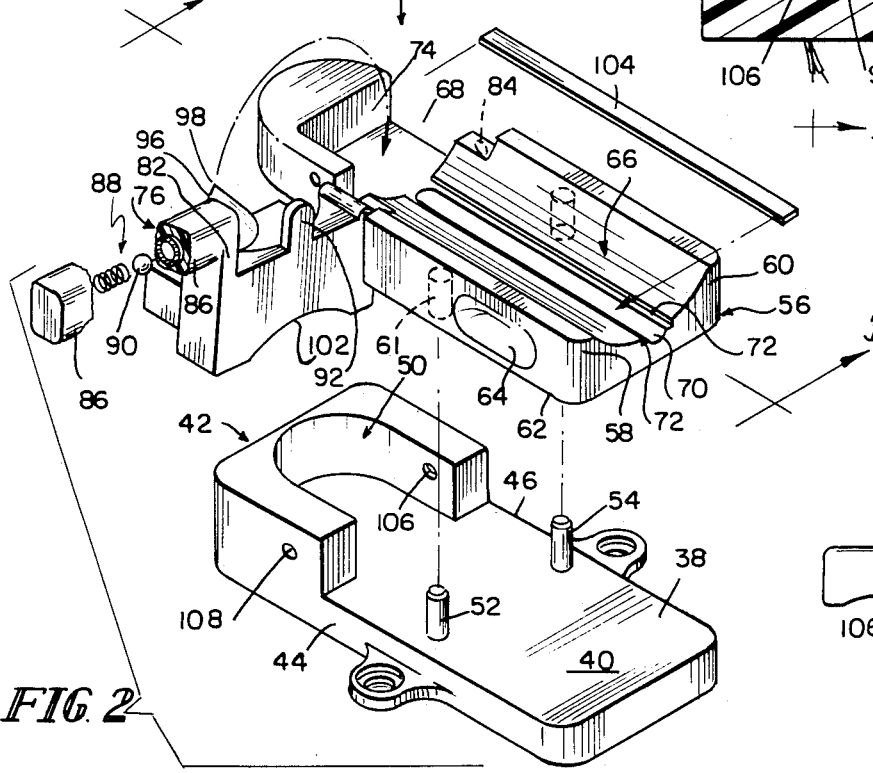
FIG. 2 is an exploded perspective view of a detail of the system of FIG. 1.
Figure 4:
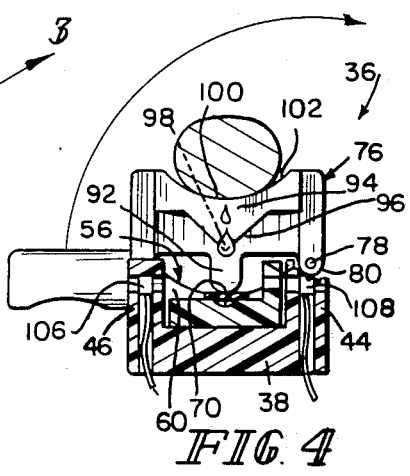
FIG. 4 is a sectional view of the detail of FIGS. 2–3 taken generally along section lines 4—4 of FIG. 3.

Turning now to FIGS. 2–4, the blood transfer assembly fixture 36 includes a mounting base 38 with a flat generally planar forward region 40 and a rear wall 42 which extends along two parallel sides 44, 46 and across the back of the mounting base 38 to define a forwardly opening region 50. Base 38 is illustratively constructed from an easily cleanable material such as, for example, ABS synthetic resin. Base 38 includes locator pins 52, 54 molded along the opposite parallel sides 44, 46 of the mounting base 38 forward of the forward terminations of wall 42.

Blood transfer assembly fixture 36 also includes a blood transfer base 56. Tapered holes 61 open into the bottom 62 of the blood transfer base 56, for receiving locator pins 52, 54, respectively to locate base 56 on the fixture base 38. Side walls 58, 60 also include finger grip recesses 64 which facilitate removal of blood transfer base 56 from fixture base 38 for cleaning. The top surface of blood transfer base 56 includes a forward generally upwardly concave region 66 and a rearward generally planar region 68. Region 68 lies generally within the region 50 formed by wall 42 when the blood transfer base 56 is positioned on locator pins 52, 54 and moved downwardly into fixture base 38.

An upwardly concave groove 70 extends rearward from the front of the blood transfer base 56. In the region 66 of the base 56, a narrow, flat land region 72 is provided between each side edge of groove 70 and the adjacent upwardly concave portion 66 of the base. The blood transfer base 56 includes a stop 74 formed rearward of the rear end of groove 70. A "funnel" 76 is hinged to the wall 58 providing the forward upwardly concave region 66 of blood transfer base 56 by a stainless steel hinge pin 78 which is press-fitted through a downwardly extending ear 80 formed on a side wall of the funnel 76, and an aligned hole provided in the side wall 58.

The opposite side wall ear 82 of funnel 76 extends downward farther onto the opposite side wall 60 forming region 66. This opposite side wall 60 is provided with a part-spherical recess 84, illustrated in broken lines in FIGS. 2-3, forming one component of a latch mechanism. Other components of the latch mechanism include an elongated handle 86 which is molded as part of the funnel 76 on ear 82, and a ball plunger mechanism including a spring 88-loaded ball 90. The ball plunger is housed within a generally right circular cylindrical hole which extends axially of the handle 86. The ball 90 engages the part-spherical recess 84 when the funnel 76 is pivoted in the direction of the arrow in FIG. 2 to latch the funnel 76 in the downward position. The funnel 76 is provided with a downwardly extending projection 92 between ears 80, 82, such that, when the funnel 76 is in its downward position and latched, the projection 92 extends to substantially the same vertical height as the land regions 72 on either side of the groove 70.

The funnel 76 includes a rearwardly facing surface 94 including a lower edge 96 terminating at a point 98 directly above the transverse center of groove 70. Surface 94 also includes an upper edge 100 formed by the intersection of surface 94 with an upwardly concave upper surface 102 of the funnel 76.

The blood transfer assembly 36 works in the following manner: a reagent-bearing test strip 104 is removed from container 28 and inserted longitudinally of blood transfer base 56 to be supported on the lands 72 on either side of groove 70. The strip 104 is inserted into the blood transfer base 56 until it encounters the stop 74 at the rearward end thereof. The funnel 76 is then pivoted downward until the ball 90 engages recess 84, locking the funnel 76 in the downward position. In this position, the projection 92 holds the strip 104 fairly securely against the lands 72, so that the position of the strip 104 is fairly fixed. The skin of the finger of the user is then pricked, using the puncture tool 22, one of heads 24 and one of lancettes 26 in known manner. The region of the finger around the opening in the skin is then worked or "milked" across the somewhat finger-shaped upwardly concave surface 102, as indicated by arrow 105 in FIG. 3, to collect blood along edge 100. The blood scraped from the skin and collected along edge 100 moves under the influence of gravity down the surface 94 and, owing to gravity and the surface tension of the blood, forms into a substantially uniformly sized droplet at the point 98 directly above the reagent-bearing region of test strip 104. The blood droplet of substantially uniform size drops from point 98 onto the reagent-bearing region of strip 104 which is positioned directly beneath point 98 by the lands 72 and stop 74.

Importantly, the user of the equipment has not had to be able to see to perform any of the operations previously described. These operations can all be performed routinely using the sense of touch only. To provide the user with an indication when a droplet of suitable portions has been deposited on the test strip 104, so that the user can stop "milking" a finger across edge 100 and prevent too-large a drop from occurring on strip 104, the monitoring base 38 is provided with a photoemitter 106 and photodetector 108. Photoemitter 106 is provided in side wall 46. Photodetector 108 is provided in side wall 44. The photoemitter 106 and photodetector 108 are aligned axially, are positioned vertically along side walls 44, 46 at sufficient heights to insure that a droplet of the appropriate size will interrupt the current of light passing between the photoemitter 106 and photodetector 108, and are both recessed into their respective side walls 44, 46 to insure minimal interference from ambient light. As will be appreciated, the droplet breaks the current of light from photoemitter 106 to photodetector 108 as it falls onto the reagent-bearing region of test strip 104. As the droplet spreads, its vertical height decreases slightly, until its surface tension balances the gravitational force tending to flatten the droplet. Accordingly, the light current between the photoemitter 106 and photodetector 108 frequently will be reestablished after the droplet of uniformed size has been deposited on test strip 104. To insure that this does not affect the operation of the system of the present invention, the photodetector 108 typically is one exhibiting some hysteresis.

The strips 104 generally are dated, since many of the reagents with which test strips are provided can age. Aging can affect the ability of the reagents in test strips to react with medically significant components of biological fluids. The calendar 30 of FIG. 1 is provided in recognition of this fact. Calendar 30 includes a number of magnetically backed numerals, four 110, 112, 114, 116 of which can be displayed at any given time on upper surface 118 of base 12. A magnetic strip is provided on surface 118 which cooperates with the backs of the numerals. The left-most numeral 110 as viewed in FIG. 1 is the more significant digit of the month in which the test strips 104 expire. Numeral 112 is the less significant digit of this month. Numeral 114 is the more significant digit of a two-digit year representation. Numeral 116 is the less significant digit of the two-digit year representation. The numerals are raised, making them easily readable by users with impaired vision.

The general operation of the system and the readout from the blood glucose monitor 32 will now be explained with reference to the electronic circuitry of FIGS. 5a-5o. The base 12 houses the photoemitter 106 and photodetector 108 as previously discussed. The illustrative photoemitter 106 is a light-emitting diode (LED) and photodetector 108 is typically an integrated circuit including a phototransistor, an amplifier and a wave-shaping circuit. The anode 132 of LED 106 is coupled through a resistor 134 to a VCC positive potential source, illustratively +5 V. The cathode 136 of LED 106 is coupled to a suitable common circuit terminal, ground. A power supply terminal 138 of photodetector 108 is also coupled to the VCC supply. The common terminal 140 of photodetector 108 is coupled to ground. A capacitor 142 is coupled across terminals 138, 140. The output terminal 144 of photodetector 108 is coupled through a resistor 146 to a conductor 148 which provides the DROP DETECT output signal.

The base 12 is provided with an unregulated battery source 150, illustratively comprising a pair of +9 V batteries in parallel. The output terminal 152 of battery 150 provides +9 V with respect to circuit ground A switch 154 controls the availability of +9 V at terminal 152. If external power is available, the plug-in power adapter 20 of FIG. 1 can be used. Adapter 20 is a 120 VAC to +9 VDC converter with a plug-in jack 155. Jack 155 disconnects battery 150 from the circuit when the jack is plugged into the switch 154 as shown in broken lines in FIG. 5a.

The battery 150 also provides power to the blood glucose monitor 32 through terminals 156, 158. FIG. 5a also illustrates terminals for signals available from the blood glucose monitor 32, if the REFLOCHECK TM monitor is used. The signals available at these terminals include a POWER ON signal available on terminal 160, a DATA signal available on terminal 162, a CLOCK signal available on terminal 164, and a common ground connection at terminal 166. When the REFLOWCHECK TM monitor is in the TEST mode, a TEST signal is available at terminal 168, and a language signal, LANG, is available at terminal 170. A terminal 172 also provides a common ground. A small speaker 174 (FIG. 5b) with conductors 176, 178 is mounted in the base 12 for communicating outputs from the system to the user.

Conductor 152 (FIG. 5a) couples battery voltage through a resistor 180 to the collector of a transistor 182. The emitter of transistor 182 is coupled to ground. The base of transistor 182 is coupled to the POWER ON terminal 160, and through a capacitor 184 to ground. Signal from the collector of transistor 182 is coupled through a series resistor 186 to the gate of a P-channel insulated gate field-effect transistor (IGFET) regulator 190. Illustratively, FET 190 may be a type IFRD 9123 FET. The source and other gate of FET 190 are coupled to conductor 152. The drain of FET 190 is coupled through a capacitor 192 to ground and provides a regulated voltage VA approximately equal to the battery voltage, e.g., +9 V. The drain of FET 190 is also coupled to an input terminal, pin 1, of an intergrated circuit voltage regulator 194, such as the type LM 7805 CT regulator. Pin 2, the ground terminal, of regulator 194 is coupled to the circuit ground. The output terminal, pin 3 of regulator 194 is coupled through a capacitor 196 to ground, and forms the regulated VCC terminal of the circuit.

The TEST terminal 168, the DROP DETECT line 148 and the LANG terminal 170 are coupled through resistors 200, 202, 204, respectively, to VCC. The DATA terminal 162 is coupled to an input terminal of an inverting amplifier 206 The output terminal of inverting amplifier 206 is coupled to an inverting input terminal of an amplifier 208. The input terminal of amplifier 206 is also coupled to ground through a resistor 210. The CLOCK terminal 164 is coupled to an input terminal of an inverting amplifier 212. The input terminal of amplifier 212 is also coupled to ground through a resistor 214.

The TEST terminal 168 is also coupled to an input terminal A1, pin 34, of a microcomputer 216, such as the Motorola MC 68705 U3L. The C1 input terminal, pin 10, of microcomputer 216 is coupled to the DROP DETECT conductor 148. The A6 terminal, pin 39, of microcomputer 216 is coupled to the LANG terminal 170. The C0 terminal, pin 9, of microcomputer 216 is coupled to the output terminal of amplifier 208. The $\overline{INT}$ terminal, pin 3, of microcomputer 216 is coupled to the output terminal of inverting amplifier 212. Terminals A2, A3, A4 and A7, pins 35, 36, 37, and 40, respectively, of microcomputer 216 are coupled through a resistor 218 to VCC. Terminals VPP and VCC, pins 7 and 4, respectively, of microcomputer 216 are also coupled to VCC. Terminals VSS and TMR/BOOT, pins 1 and 8, respectively, of microcomputer 216 are coupled to the circuit ground. The RST terminal, pin 2 of microcomputer 216 is coupled through a capacitor 220 to ground. A 4.0 MHz crystal 222 is coupled across the EXTAL and XTAL terminals, pins 5 and 6, respectively, of microcomputer 216. A capacitor 224 is coupled between pin 5 of microcomputer 216 and ground.

The A5 terminal, pin 38, of microcomputer 216 is coupled to an input terminal of an inverting amplifier 226. The input terminal of amplifier 226 is also coupled to ground through a resistor 228. The output terminal of amplifier 226 is coupled to a gate electrode of a P-channel IGFET, whose source and other gate are connected to VCC and whose drain provides a standby voltage VSBY. The B7, B6, B5, B4, B3, B2, B1, B0, A0, C2 and C3 terminals, pins 32, 31, 30, 29, 28, 27, 26, 25, 33, 11 and 12, respectively, of microcomputer 216 are coupled, respectively, to (FIG. 5b) terminals A8, A7, A6, A5, A4, A3, A2, A1, $\overline{ALD}$, $\overline{LRQ}$ and SBY, pins 10, 11, 13, 14, 15, 16, 17, 18, 20, 9 and 8, respectively, of a speech controller integrated circuit 230. Illustratively, speech controller integrated circuit 230 is a type SP0256-AL2 integrated circuit speech controller microprocessor available from General Instruments. The VSS terminal of circuit 230 is coupled to ground. The SE, TEST and VD1 terminals, pins 19, 22, 23, respectively, of circuit 230 are coupled to VCC. The VDD terminal, pin 7, of circuit 230 is coupled to VSBY (FIG. 5a).

The SER OUT, SER IN, C1, C2, C3 and ROM DISABLE terminals, pins 12, 21, 4, 5, 6 and 3, respectively, of circuit 230 are coupled, respectively, to the SER IN, SER OUT, C1, C2, C3 and ROM $\overline{ENA}$ terminals, pins 25, 9, 15, 14, 13 and 8, respectively, of a serial-to-parallel converter integrated circuit 232 such as the SPR 000 available from General Instruments. The VDD and CS1 terminals, pins 26 and 6, respectively, of circuit 232 are coupled to VSBY. The VSS and $\overline{CS2}$ terminals, pins 1 and 7, respectively, of circuit 232 are coupled to ground. The ROM CLK terminal, pin 27, of circuit 232 is coupled to the ROM CLK terminal, pin 26, of speech controller 230.

Speech ROM capacity is provided by a speech ROM 234, such as the type 27128 speech ROM available from Seeq. The connections between the serial-to-parallel converter 232 and speech ROM 234 are as follows: terminals D0-D7, pins 35-28 respectively, of circuit 232 are coupled, respectively, to terminals O0-O7 pins 11, 12, 13, 15, 16, 17, 18 and 19, respectively, of speech ROM 234. Terminals A0-A13, pins 24, 23, 22, 21, 20, 19, 18, 17, 16, 12, 11, 5, 3 and 40, respectively, of circuit 232 are coupled, respectively, to terminals A0-A13, pins 10, 9, 8, 7, 6, 5, 4, 3, 25, 24, 21, 23, 2 and 26, respectively, of speech ROM 234. Terminals VPP, VCC and PGM, pins 1, 28 and 27, respectively, of speech ROM 234 are coupled to VSBY. Terminals $\overline{CE}$, $\overline{OE}$ and GND, pins 20, 22, and 14, respectively, of speech ROM 234 are coupled to circuit ground.

A 3.12 MHz crystal 236 is coupled across terminals OSC1 and OSC2, pins 27, 28, respectively, of speech controller 230. These terminals are also coupled to ground through capacitors 238. A parallel circuit including a resistor 240 and diode 242 is coupled between VSBY and the $\overline{RST}$ terminal, pin 2, of speech controller 230. The cathode of diode 242 is coupled to VSBY and its anode is coupled to ground through capacitor 244. A similar circuit including a parallel resistor 246 and diode 248 is coupled between VCC and the $\overline{SBY\ RST}$ terminal, pin 25, of speech controller 230. The cathode of diode 248 is coupled to VCC and its anode is coupled to ground through a capacitor 250.

The audio frequency analog output of the speech controller circuit 230 appears at its DAC OUT terminal, pin 24. This signal is coupled through a multiple-section R-C filter including resistor 252, resistor 254, capacitor 256 and resistor 258 in series, to the + input terminal, pin 3, of an amplifier 260, such as the type LM386-4. The junction of resistors 252 and 254 is coupled to ground through a capacitor 262. The junction of resistor 254 and capacitor 256 is coupled to ground through a capacitor 264. The junction of capacitor 256 and resistor 258 is coupled to ground through a resistor 266. Pin 3 of amplifier 260 is coupled to ground through a resistor 268. The − input terminal, pin 2, of amplifier 260 is coupled to ground. Pins 12, 8 of circuits 216 (FIG. 5a), 230 (FIG. 5b), respectively, are coupled to an input terminal of an inverting amplifier 270. The output terminal of amplifier 270 is coupled to an inverting input terminal of an amplifier 272. The output terminal of amplifier 272 is coupled through a resistor 274 to the base of a muting transistor 276, and through a capacitor 278 to ground. The emitter of transistor 276 is coupled to ground. Its collector is coupled to pin 1 of amplifier 260 and through a capacitor 280 to pin 8 of amplifier 260. Pin 6 of amplifier 260 is coupled to VA. Pin 7 of amplifier 260 is coupled through a capacitor 282 to ground and pin 4 of amplifier 260 is coupled to ground.

Figure 5A:
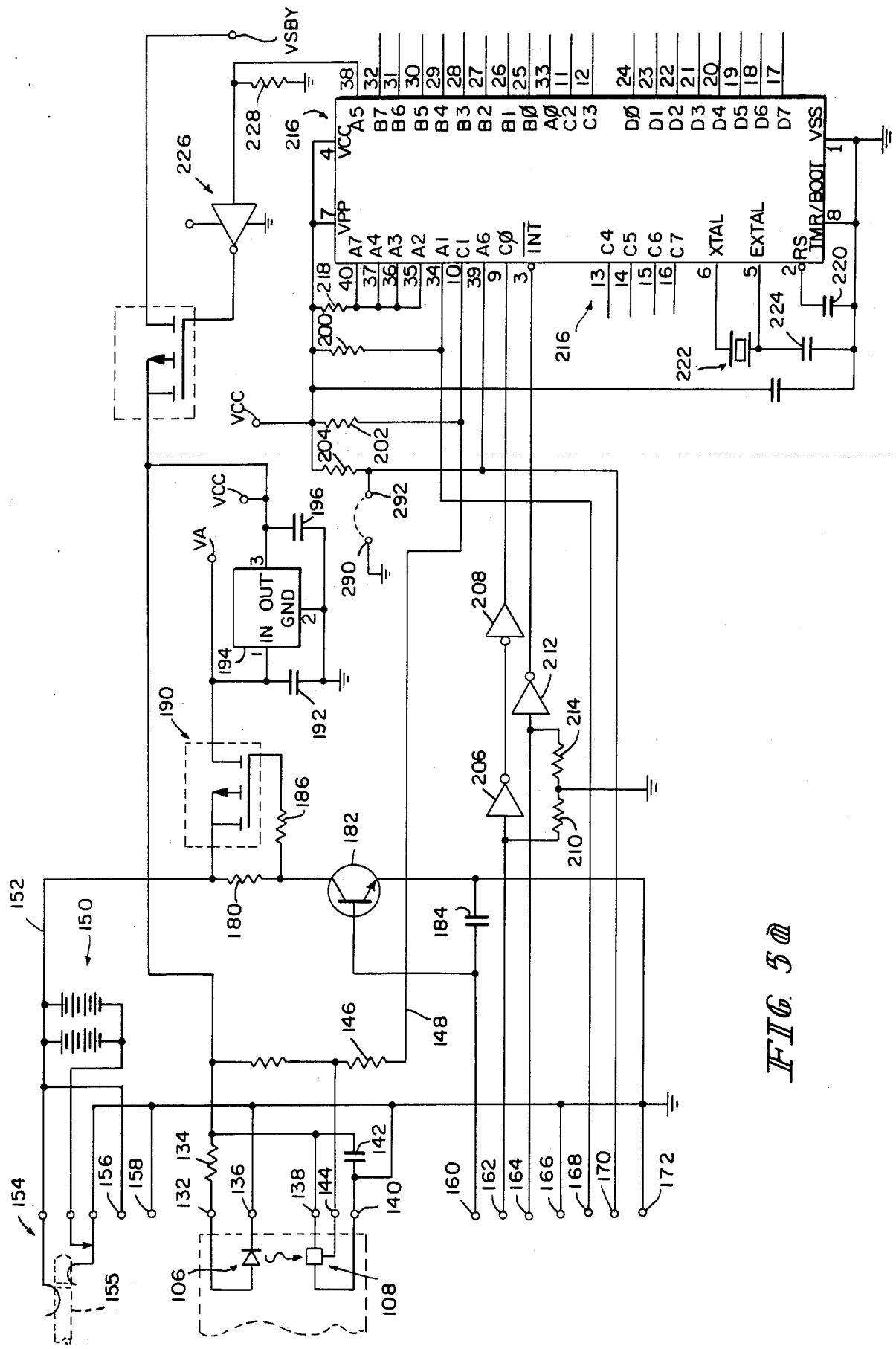
FIGS. 5a–5b are partly block and partly schematic electrical circuit diagrams of suitable electrical circuit realizations of portions of the system illustrated in FIG. 1.
Figure 5B:
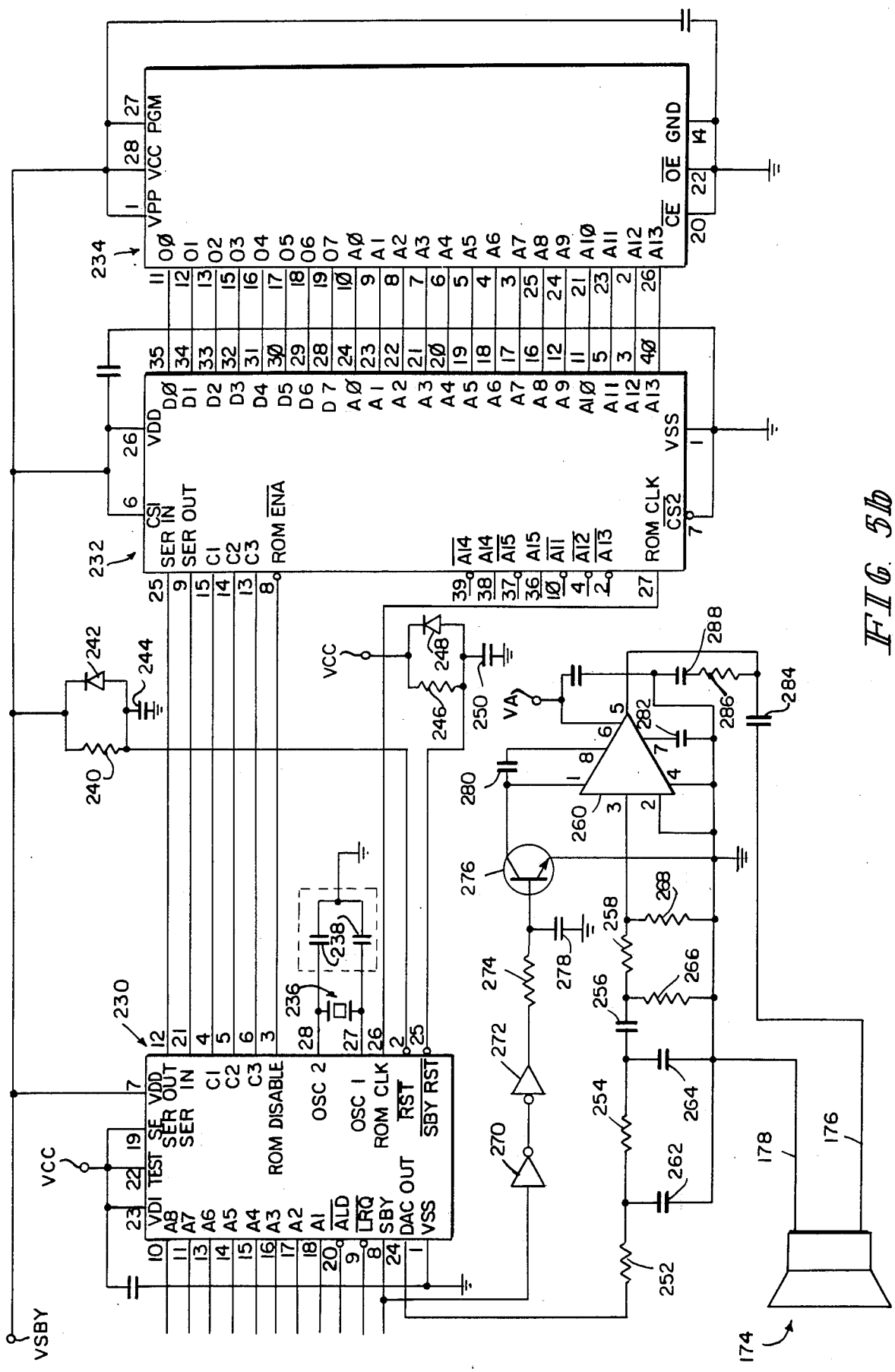

The output terminal, pin 5, of amplifier 260 carries amplified audio information, such as the glucose content as read by the blood glucose monitor 32 and transmitted to the circuitry of FIGS. 5a–5b through the DATA terminal 162. The speech controller circuitry also generates an audible signal when a droplet of the substantially uniform size has dropped onto the test strip 104 so that the user can stop supplying blood to the strip. The speech controller circuitry then times the interval between placement of the blood droplet on the test strip 104 and the end of the reaction interval, at which time the speech controller instructs the user to wipe the blood droplet off the test strip and insert the test strip into the blood glucose monitor 32 for reading of the blood glucose level.

The various CLK, and other undesired, frequencies generated in the speech controller and related circuitry are removed by the multiple-section R-C filter on the input terminal, pin 3 of amplifier 260. Audio frequency output is provided to the speaker conductors 176, 178 through DC blocking capacitor 284. The output terminal, pin 5, of amplifier 260 is also coupled to ground through a series R-C circuit 286, 288.

The circuit is provided with a language jumper terminal pair 290, 292. Terminal 290 is coupled to ground. Terminal 292 is coupled to LANG terminal 170. Application of a conductor across terminals 290, 292 grounds terminal A6, pin 39, of microcomputer 216. If the microcomputer 216 and speech controller 230 are programmed to provide speech in multiple languages, such as, for example, English and German, this provides a handy technique for converting from one language to the other.

What is claimed is:

1. A blood transfer apparatus comprising
   a base for supporting, a test strip carrying a reagent for reacting with a medically significant component in blood to produce a visual indication on such a test strip of the concentration of such a component in blood,
   funnel means for forming a blood droplet from a pricked finger, and
   means for pivotally connecting the funnel means to the base for pivotal movement between a test orientation engaging a test strip supported on the base in a blood droplet-receiving position and a release orientation away from a test strip supported on the base.

2. The blood transfer apparatus of claim 1 wherein the base includes at least one stationary wall for aligning a test strip supported on the base in a predetermined position when the funnel means is in its test orientation so that a portion of such a test strip is disposed underneath the funnel means to receive a blood droplet therefrom.

3. The blood transfer apparatus claim 1 wherein the funnel means includes means for dispensing a blood droplet and a separate projection for engaging a test strip supported on the base when the funnel means is in its test orientation to retain such a test strip against the base in the blood droplet-receiving position undereath the dispensing means, the projection permitting removal and replacement of a test strip when the funnel means is in its release orientation in spaced-apart relation to the base.

4. The blood transfer apparatus of claim 3 wherein the means for dispensing a blood droplet includes a transfer surface for conducting blood toward a test strip supported on the base when the funnel means is in its test orientation, the transfer surface including an upper edge across which a pricked finger is drawn to deposit blood onto the transfer surface and a lower edge terminating at a point so that blood flowing across the transfer surface forms into a uniformly sized droplet at the point owing to gravity and the surface tension of blood.

5. The blood transfer apparatus of claim 4 wherein said point is situated in spaced-apart aligned relation to a test strip supported on the base when the funnel means is in its test orientation to position a droplet falling from the point in alignment with such a test strip so that a falling droplet is deposited thereon for analysis of a medically significant component thereof.

6. The blood transfer apparatus of claim 4 wherein the funnel means further includes an upper concave surface with a curved contour corresponding generally to the exterior shape of a portion of a finger, and the upper concave surface and the transfer surface intersect to define said upper edge.

7. The blood transfer apparatus of claim 4 wherein the base includes a photoemitter and a photodetector situated in spaced-apart relation so that a falling blood droplet from the point interrupts a current of light from the photoemitter to the photodetector and thereby provides a signal that droplet formation and deposit is complete.

8. A blood transfer apparatus for forming a blood droplet from a pricked finger and for positioning said droplet for analysis of a medically significant component thereof, the apparatus comprising
   a droplet-forming portion comprising a first surface across which blood flows under the influence of gravity, the first surface including first and second vertically spaced-apart upper and lower edges, the lower edge terminating at a point and the upper edge having an upward concave contour corresponding generally to the cross section of a finger, across which upper edge a finger is drawn to deposit blood on the first surface, a base comprising means providing a second surface disposed directly beneath the point to receive a droplet formed as blood flows across the first surface toward the point where, owing to gravity and the surface tension of blood, the blood forms into a uniformly sized droplet which falls onto the second surface, said means providing the second surface comprising means for holding a test strip carrying a reagent for reacting with a medically significant component of blood to produce a visual indication on such a test strip of the concentration of such a component in blood, and means for pivotally connecting the droplet-forming portion to the base, the droplet-forming portion being pivotable between a first blood droplet forming and positioning orientation engaging a test strip supported on the base and a second test strip removal and replacement orientation with respect to the base.

9. The blood transfer apparatus of claim 8 wherein the droplet-forming portion further comprises means for engaging a test strip when the droplet-forming portion is in the blood droplet forming and positioning orientation.

10. The blood transfer apparatus of claim 9 wherein the base is provided with a photoemitter and photodetector positioned on the base so that a blood droplet falling from the point onto the second surface will interrupt a current of light from the photoemitter to the photodetector and thereby provide a signal that droplet formation and positioning is complete.

* * * * *